United States Patent [19]

Krcma et al.

[11] Patent Number: 5,184,500

[45] Date of Patent: Feb. 9, 1993

[54] GAS DETECTOR

[75] Inventors: Jan Krcma, Elk Grove Village; Terry A. Batt, Elmhurst, both of Ill.

[73] Assignee: J and N Associates, Inc., Valparasio, Ind.

[21] Appl. No.: 496,333

[22] Filed: Mar. 20, 1990

[51] Int. Cl.⁵ .................................... G01N 27/00
[52] U.S. Cl. ................................... 73/23.2; 364/498
[58] Field of Search ................... 73/23.2, 23.21, 1 G; 364/498, 571.01–571.08

[56] References Cited

U.S. PATENT DOCUMENTS

| | | | |
|---|---|---|---|
| 1,778,508 | 10/1930 | Peoples | 73/755 X |
| 2,763,838 | 9/1956 | McConnell | 324/140 |
| 3,064,478 | 11/1962 | Schafer | 73/708 X |
| 3,077,561 | 2/1963 | Revesz | 73/708 X |
| 3,153,577 | 10/1964 | McCully et al. | 422/96 X |
| 3,161,821 | 12/1964 | Price et al. | 324/706 X |
| 3,191,068 | 6/1965 | Robb, Jr. | 307/88.5 |
| 3,237,181 | 2/1966 | Palmer | 422/96 X |
| 3,351,927 | 11/1967 | Stinson | 340/248 |
| 3,375,700 | 4/1968 | Hübner | 73/23.2 X |
| 3,466,552 | 9/1969 | Sels | 328/147 |
| 3,600,606 | 8/1971 | Clor, Jr. | 307/235 |
| 3,792,342 | 2/1974 | Ogawa et al. | 324/706 X |
| 3,895,611 | 6/1975 | Endo et al. | 123/487 |
| 3,898,462 | 8/1975 | Ishida et al. | 250/344 |
| 4,002,429 | 1/1977 | Bartovsky et al. | 422/96 |
| 4,034,743 | 7/1977 | Greenwood et al. | 364/413.03 X |
| 4,045,296 | 8/1977 | Sternberg | 195/103.5 |
| 4,088,985 | 5/1978 | Saito et al. | 340/605 |
| 4,231,249 | 11/1980 | Zuckerman | 340/632 X |
| 4,305,724 | 12/1981 | Micko | 422/94 X |
| 4,320,664 | 3/1982 | Rehn et al. | 73/708 |
| 4,337,665 | 6/1982 | Sato et al. | 73/766 |
| 4,352,087 | 9/1982 | Wittmaier | 340/632 |

(List continued on next page.)

FOREIGN PATENT DOCUMENTS

| | | | |
|---|---|---|---|
| 207053 | 10/1985 | Japan | 73/23.2 |
| 231150 | 11/1985 | Japan | 73/23.2 |
| 241458 | 10/1988 | Japan | 73/23.2 |
| 1-307636 | 12/1989 | Japan | 73/23.2 |

(List continued on next page.)

OTHER PUBLICATIONS

A four-page brochure or Bacharach Instrument Co. entitled "The Ultra Series of Portable Gas Detectors" May 1979.
A five-page product data brochure of Bacharach, Inc. entitled "Combustible Gas Indicators: Model L. Sniffer" Dec. 1987.
A one-page product data sheet of United Technologies/Bacharach entitled "Sniffer ® 301 Portable Combustible Gas Detector" published by Mar. 1992.
A six-page brochure of GasTech, Inc. entitled "GasTech-The Trusted Name in Gas Detection" Apr. 1987.
A two-page product brochure of GasTech, Inc. entitled "Model 1238 GasTechtor Hydrocarbon Surveyor Portable PPM/LEL Combustible Survey Meter" published by Mar. 1992.
A two-page product bulletin of Dynamation Incorporated entitled "COMBO 034 Combination Combustible,

(List continued on next page.)

Primary Examiner—Tom Noland
Attorney, Agent, or Firm—Marshall, O'Toole, Gerstein, Murray & Bicknell

[57] ABSTRACT

A battery-powered gas detector comprises a gas sensor coupled to a current source and a power supply. The power supply generates a relatively high voltage when the gas sensor is warming up and a relatively low voltage after the sensor has warmed up. The gas sensor, which is responsive to the presence of a gas, is coupled to an amplifier having a variable sensitivity circuit. The amplifier is connected to a microprocessor that determines the concentration of the sensed gas and provides a visual indication of the concentration on a display. The gas detector can sense the presence of a variety of different gases. The gas concentration of the sensed gas is determined based upon the magnitudes of a gas sensing signal generated by the amplifier, a calibration signal generated during a calibration routine when the detector is in a controlled environment, and an error signal generated when the detector is in a no-gas environment.

23 Claims, 5 Drawing Sheets

U.S. PATENT DOCUMENTS

| | | | |
|---|---|---|---|
| 4,385,491 | 5/1983 | Sakurai et al. | 123/440 X |
| 4,422,073 | 12/1983 | Winner | 340/870.21 |
| 4,464,653 | 8/1984 | Winner | 340/501 |
| 4,476,706 | 10/1984 | Hadden et al. | 73/1 G |
| 4,480,252 | 10/1984 | Buonavita | 340/632 |
| 4,532,442 | 7/1985 | Black | 307/520 |
| 4,551,425 | 11/1985 | Zemel | 435/4 |
| 4,578,762 | 3/1986 | Wong | 250/343 X |
| 4,601,809 | 7/1986 | Kitahara | 204/406 |
| 4,613,770 | 9/1986 | Raab | 307/350 |
| 4,651,559 | 3/1987 | Horigome et al. | 73/40.5 R |
| 4,814,643 | 3/1989 | Ishihara et al. | 307/355 |
| 4,914,720 | 4/1990 | Knodle et al. | 250/343 |
| 4,918,311 | 4/1990 | Rogers | 250/343 |
| 5,060,505 | 10/1991 | Tury et al. | 73/1 G |

FOREIGN PATENT DOCUMENTS

| | | | |
|---|---|---|---|
| 1350579 | 11/1987 | U.S.S.R. | 73/23.2 |
| 1425825 | 2/1976 | United Kingdom | |
| 2082860 | 3/1982 | United Kingdom | 73/23.2 |

OTHER PUBLICATIONS

Toxic & Oxygen Deficiency Alarm" published by Mar. 1992.

A one-page product sheet of Scott entitled "D-17 Vapolert" Jun. 1976.

A four-page brochure of Scott entitled "Portable Instruments, 'D' Series, Intrinsically Safe" Jan. 1977.

A two-page brochure of Bacharach Instrument Co. entitled "Portable Gas Analyzers for Combustible Gas Hazard and Oxygen Deficiency Tests" Sep. 1973.

A one-page product specification of Analysis & Survey Equipment, Inc. entitled "Onmark ® Combustible Gas Indicator" published by Mar. 1992.

An undated two-page brochure entitled "GMI Gasurveyor—A New Concept in Gas Detection" published by Mar. 1990 by Gas Measurement Instruments Ltd of Renfrew, Scotland.

An undated two-page brochure entitled "GMI Gasurveyor—Calibration Systems" published by Mar. 1990 by Gas Measurement Instruments Ltd of Renfrew, Scotland.

A four-page brochure entitled "TLV Sniffer High-Sensitivity, Combustible Gas Indicator" May 1987 by Bacharach of Pittsburgh, Pa.

A Davis Instruments catalog, p. 96, entitled "Microprocessor Gas Detector" published by Mar. 1990.

GAS DETECTOR

Background of the Invention

The present invention relates to a gas detector, and more particularly to a gas detector having improved electronic processing and power-saving features.

Gas detectors are used to sense the presence of gases, often for the purpose of determining whether combustible or otherwise harmful gases are present. Such gas detectors are portable and preferably hand-held to allow the user mobility so that various areas can be tested. Such gas detectors may generate audio or visual alarms if gas is present in a dangerous concentration.

Gas detectors of the type described above may be battery-powered and may incorporate gas sensing elements that require a relatively high voltage during their warm-up period. Such gas detectors have therefore been provided with a power supply that supplies the required high voltage to the sensor during warm-up and afterwards. Although the relatively high voltage is necessary during warm-up, the provision of such a voltage after sensor warm-up is undesirable in that it causes an undesirable amount of drain on the battery.

A battery-powered gas detector typically includes an on-off switch requiring the user turn off the detector. If the user forgets to turn off the device, the battery would be unnecessarily drained, thus requiring more frequent replacement of the battery. Moreover, when powered up, a conventional gas detector may require an unduly large amount of current from the battery.

Some gas detectors operate by generating two electrical signals, a variable signal that relates to the concentration of the gas sensed and a reference signal that is not responsive to the gas sensed. Detectors of this type may utilize an analog-to-digital (A/D) converter to convert the variable signal and the reference signal, which are analog, to digital form. In general, it is desirable to use A/D converters having high resolution. However, the cost of A/D converters generally increases as their resolution increases. It would be desirable to achieve increased A/D converter resolution without an accompanying increase in cost.

Previous gas detectors may have the capability of sensing the presence of a number of different gases. However, such gas detectors may be unnecessarily complicated, thus raising their cost.

SUMMARY OF THE INVENTION

The present invention relates to a gas detector having a gas sensor, a power supply coupled to the gas sensor, an amplifier circuit coupled to the gas sensor, and a signal processing circuit, such as a microprocessor, coupled to the amplifier circuit for processing the signals generated by the amplifier circuit.

According to one feature of the present invention, the amplifier circuit generates a pair of gas sensing signals, each of which is responsive to the concentration of the sensed gas, and supplies those signals to an A/D converter circuit in the signal processing circuit. The A/D converter generates two binary counts, one for each of the gas sensing signals, and the two binary counts are supplied to a difference circuit that generates a signal relating to the concentration of the sensed gas based upon the difference between the two binary counts. One advantage of this feature of the invention is that since two gas sensing signals are provided to the A/D converter circuit, both of the signals being related to the concentration of the gas sensed, the resolution available from the A/D converter circuit is increased.

Another feature of the invention relates to the provision of a power supply that generates two different voltage levels Gas sensors of the type used in the gas detector require a higher voltage during their warm-up period than that required for normal operation after they are warmed up. The power supply in accordance with this feature of the invention generates the required relatively high voltage from a source of battery power while the gas sensor is warming up and a relatively low voltage after the sensor has warmed up. The initial high voltage may be about three times as high as the subsequent low voltage. As a result of the reduction in power supply voltage, the drain on the gas detector battery may be reduced.

Another feature of the invention relates to conserving battery power. According to this feature, the power supply is automatically shut off a predetermined period of time after the power supply is turned on by the user. The power supply has a circuit that generates a "turn-on" signal when the user turns the power supply on, and the gas detector generates a "power-off" signal a predetermined time after the occurrence of the turn-on signal. The power supply also includes a field-effect transistor which, when turned on, allows a pair of battery terminals to supply power to the power supply. Since the voltage drop across the source and drain terminals of the field-effect transistor is minimal during operation of the gas detector, the current requirement of the detector is minimized. Also, battery power is not wasted due to the detector being inadvertently left on for long periods of time.

In accordance with another feature of the invention, the amplifier of the gas detector is provided with a variable sensitivity circuit that can be programmed to provide many different sensitivity values. The purpose of providing the variable sensitivity circuit is to allow the detector to efficiently sense the presence and determine the concentration of many different gases. A gas detector with a fixed-sensitivity amplifier would not necessarily be able to accurately sense the presence of many gases, and even if it could do so, its resolution would be limited.

Another feature of the invention relates to a method of sensing gas which includes a zeroing routine and a gas sensing routine. In the zeroing routine, an error signal is generated when the gas detector is in an environment substantially free of the gas to be measured. After the error signal is generated, the gas detector adjusts the concentration of the gas sensed in the environment where gas is present based on the magnitude of the error signal. As a result, inaccuracies in the sensed gas concentration due to temperature and humidity effects are avoided.

These and other features and advantages of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENTS

Figure 1:
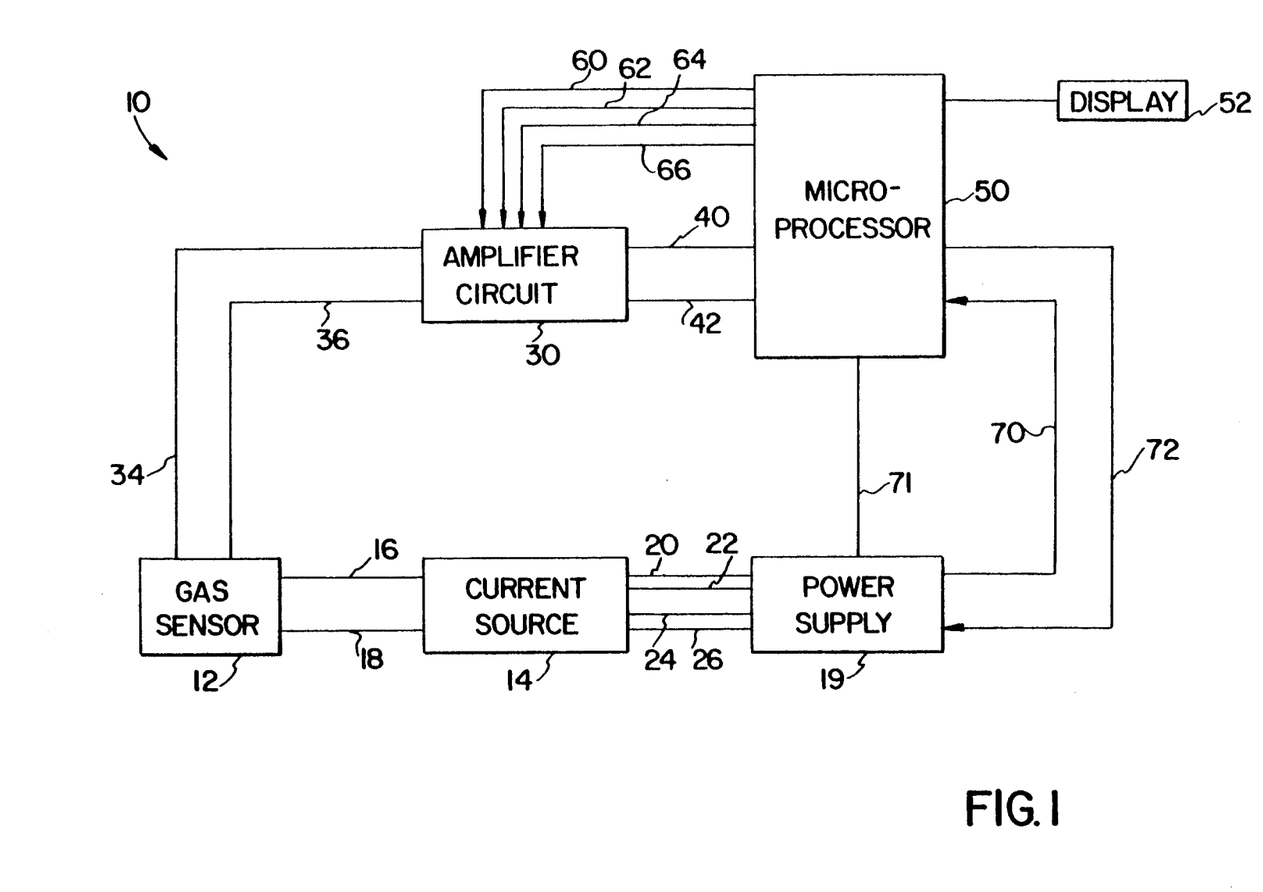
FIG. 1 is a block diagram of a gas detector in accordance with the invention having a gas sensor, a current source, a power supply, an amplifier circuit, and a microprocessor.

A block diagram of the electronics of a gas detector 10 in accordance with the invention is shown in FIG. 1. The gas detector is a portable, battery-powered detector that is designed to be hand-held. The gas detector can detect the presence of any number of gases such as natural gas, gasoline vapors, hydrogen, methane, carbon dioxide, etc. and can generate an alarm signal via an LED or beeper to warn the user that the concentration of the gas has reached a dangerous level. The detector can also generate a numeric display of the gas concentration.

The gas detector 10 includes a gas sensor 12 that is responsive to the presence of gas. The gas sensor 12 is coupled to a current source 14 via a pair of lines 16, 18. The current source 14, which supplies a constant current to the sensor 12, provides relatively fast warm-up of the detector, higher accuracy, and more stability. The current source 14 is coupled to a power supply 19 via a first pair of lines 20, 22 and a second pair of lines 24, 26. The gas sensor 12 is coupled to an amplifier circuit 30 via a pair of lines 34, 36.

When operating, the gas sensor 12 is provided with a constant current from the source 14, and in the presence of gas, the sensor 12 generates voltage signals on the lines 34, 36. The amplifier circuit 30 amplifies the signals and, as described in more detail below, generates a pair of opposite-going signals on a pair lines 40, 42 coupled to a microprocessor 50. From the signals on lines 40, 42, the microprocessor 50 generates a signal relating to the concentration of the gas sensed. The microprocessor 50 is coupled to a visual display 52, which may be an LCD display, and causes the display 52 to generate a visual indication of the gas concentration sensed and alarm indications when an alarm condition is present.

The microprocessor 50 is connected to the amplifier circuit 30 via four lines 60, 62, 64, 66. As described in more detail below, the microprocessor 50 transmits digital control signals to the amplifier 30 via these four lines 60, 62, 64, 66 to vary the sensitivity of the amplifier circuit 30. Changing the sensitivity of the amplifier 30 allows the detector 10 to accurately determine the concentrations of different gases.

The microprocessor 50 is also connected to the power supply 19 via three lines 70, 71, 72 which control the supply of power to the gas detector. Power is transmitted from the power supply 19 to the microprocessor 50 via the line 71. As described in more detail below, when the power is turned on, the power supply 19 transmits a digital signal to the microprocessor 50 via the line 70. Then, a predetermined time after the power supply 19 is turned on, a "power-off" signal is transmitted from the microprocessor 50 to the power supply 19 via the line 72 to automatically turn off the power.

Figure 2:
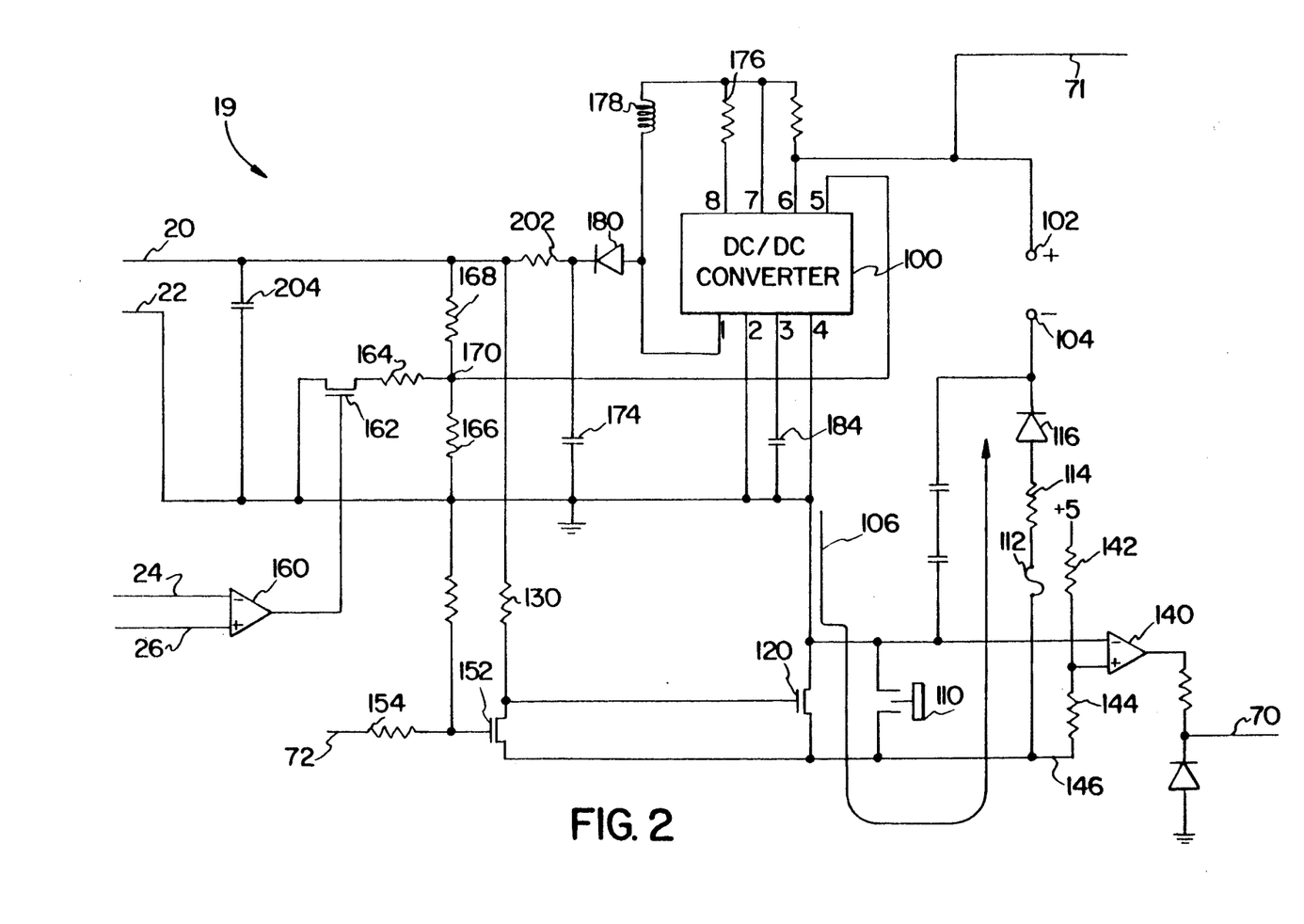
FIG. 2 is a circuit diagram of the power supply of FIG. 1.

FIG. 2 is a circuit diagram of the power supply 19 shown schematically in FIG. 1. Referring to FIG. 2, the power supply 19 includes a DC/DC converter 100 directly connected to a positive battery terminal 102. The DC/DC converter 100 converts the battery voltage of about six volts, which may be provided by four 1.5 volt AA batteries connected in series, to a voltage ranging from about seven volts to about 20 volts, depending upon whether the sensor 12 is warmed up. The DC/DC converter 100 is a conventional circuit such as an MC33063A commercially available from Motorola. The negative battery terminal 104 is coupled to the DC/DC converter 100 via a current path, indicated by an arrow 106, that includes a pushbutton 110, a fuse 112, a resistor 114, and a diode 116.

One feature of the power supply circuit 19 is an automatic shutoff feature that turns off the power supply 19 a predetermined period of time after it is turned on. This predetermined period of time, which may be ten minutes for example, is programmable so that various shutoff times can be selected. The power supply 19 is turned on by depressing the pushbutton 110. When depressed, the pushbutton 110 connects the DC/DC converter 100 to the negative battery terminal 104 via the current path indicated by the arrow 106. As a result, power is supplied to the DC/DC converter 100.

As soon as the DC/DC converter 100 is connected to the negative battery terminal 104, the converter 100 generates a relatively high voltage on the line 20 coupled to the current source 14. The gate of a field-effect transistor (FET) 120 is connected to the line 20 through a resistor 130. When the voltage on the line 20 goes high, the voltage supplied to the gate of the FET 120 also goes high and turns on the FET 120, thus rendering it conductive. As a result, the FET 120 provides a second current path in addition to the initial current path 106. This second current path is nearly the same as the current path 106, except that the second current path includes the FET 120 instead of the pushbutton 110.

The use of a FET in the second current path is advantageous because when the FET 120 is turned on, the voltage across its source and drain terminals is relatively small. As a result, the current drain from the battery is minimized and the life of the battery prolonged.

The pushbutton 110, which may be a momentary switch, is spring-biased to its non-depressed position and only enables the current path 106 when it is depressed. Thus, as soon as the user lets go of the pushbutton, it returns to its non-depressed position and the current path 106 is broken. However, since the second current path is established as soon as the pushbutton 110 is depressed, the DC/DC converter 100 remains connected to the battery terminals 102, 104 in its powered-up state.

The power supply 19 is turned off by the microprocessor 50 after a predetermined period of time. When the pushbutton 110 is depressed, a comparator 140 transmits a "turn-on" signal to the microprocessor 50 via the line 70, by providing a high voltage on the line 70, indicating that the power supply 19 has just been turned on. In particular, the noninverting input of the comparator 140 is connected to the junction of a pair of resistors 142, 144 which act as a voltage divider, the resistor 142 being connected to a predetermined positive voltage, five volts for example. When the pushbutton 110 is depressed and the detector 10 is powered up, the noninverting input of the comparator 140 has a higher voltage than that on the line 146, while the inverting input voltage is equal to that on the line 146 because of the short circuit provided by the pushbutton 110. As a result, since the voltage at the inverting input is less than the voltage at the noninverting input, the comparator 140 will output a relatively high voltage, indicating that the pushbutton is depressed.

When the pushbutton 110 is released, the FET 120 is conductive and thus has a voltage drop across its source and drain terminals. The resistance value of the resistor 144 is chosen to be small compared with the resistance value of the resistor 142 so that the noninverting input of the comparator 140 will be at a slightly higher voltage than the line 146, for example 15 millivolts. As a result, when the FET 120 conducts, the voltage across the FET 120 will exceed the voltage across the resistor 144, and thus the voltage at the inverting input will be larger than the voltage at the noninverting input. Accordingly, the comparator 140 will generate a relatively low voltage, indicating that the pushbutton 110 is not depressed.

The microprocessor 50 has an internal timer 150 (shown only in FIG. 3) that begins timing upon receipt of the "turn-on" signal via the line 70. The turn-on signal is generated at power-up as a result of pressing the pushbutton 110. The power-up signal may also be generated by pressing the pushbutton 110 after initial power-up to restart the predetermined period of time for which the detector is powered and thus increase the length of time that the detector is on. After the timer 150 has finished timing, it sends a "power-off" signal to the power supply 19 via the line 72. As shown in FIG. 2, the line 72 is coupled to the base of a FET 152 via a resistor 154. When the "power-off" signal is activated by the timer 150, the FET 152 is turned on so that it conducts, causing a relatively low voltage to be transmitted to the gate of the FET 120, thus turning off the FET 120. As a result, since the second current path through the FET 120 is extinguished, the DC/DC converter 100 becomes disconnected to the negative battery terminal 104, and the power supply 19 is turned off.

Figure 3:
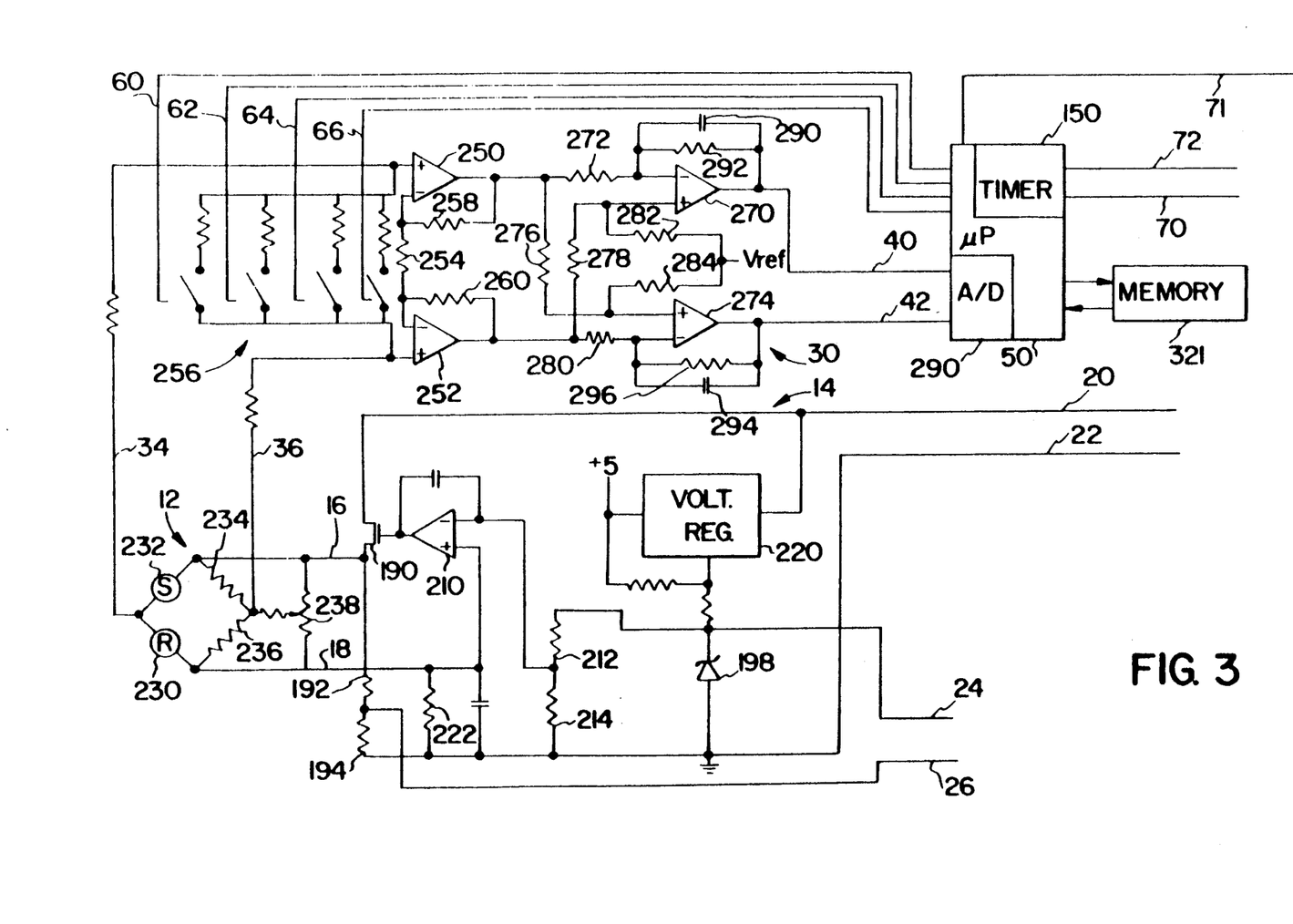
FIG. 3 is a circuit diagram of the gas sensor, the current source, the amplifier circuit, and the microprocessor of FIG. 1.

The timer 150, which is an interrupt CPU timer, may be implemented in various ways, including, for example, a binary up or down counter in hardware or as a computer program routine that acts as a timer.

If the pushbutton 110 is depressed during the middle of the predetermined power-on period, the timer 150 may be implemented such that it will be reset, thus restarting the predetermined power-on period.

During operation, the user of the gas detector 10 simply depresses the pushbutton 110 once and uses the detector to determine the concentration of gas present. The user need not turn the detector off since that is done automatically after a predetermined period of time, thereby extending battery life.

The voltage provided by the DC/DC converter 100 to the current source 14 via the line 20 varies from about 20 volts when the gas sensor 12 is warming up to about seven volts after the sensor has been warmed up. During warm-up, the sensor requires a higher voltage in order to heat an internal heater within the sensor. After the sensor has been warmed up, the higher voltage is no longer necessary. Reducing the voltage after the sensor warms up conserves battery power since less power is needed to provide a lower voltage.

The magnitude of the voltage provided by the DC/DC converter 100 is controlled by a voltage control circuit comprising a comparator 160 having an output coupled to the gate of a FET 162 provided in series with a resistor 164. The FET 162 and the resistor 164 are in parallel with a resistor 166, and that parallel combination is in series with a resistor 168. The resistors 164, 166, 168 act as a voltage divider and divide down the voltage generated by the DC/DC converter 100 across the lines 20, 22. The DC/DC converter 100 senses the divided voltage at a junction 170 of the resistors 166, 168 and uses the sensed voltage to vary its output in a manner described in more detail below.

The voltage at the junction 170 varies, depending upon whether the FET 162 is conductive or nonconductive. It should be appreciated that when the FET 162 is conductive, there is a current path through the resistor 164, and the resistor 164 is effectively placed in parallel with the resistor 166, thus reducing the voltage at the junction 170 since the combined parallel resistance of the resistors 164 and 166 is less. When the FET 162 is nonconductive, there is no current path through the resistor 164, and thus the resistor 164 is not placed in parallel with the resistor 166, thus not reducing the voltage at the junction 170. As a result, the junction 170 voltage when the FET 162 is on is lower than the junction 170 voltage when the FET 162 is off.

The DC/DC converter 100 comprises an internal oscillator controlled by an internal feedback circuit. The oscillator generates current pulses that are provided to charge up a capacitor 174. The pulses are provided to the capacitor 174 via a resistor 176, an inductor 178 and a diode 180. The voltage across the capacitor 174, and thus the voltage supplied to the current supply 14 via the lines 20, 22, is controlled by controlling the oscillation of the internal oscillator of the converter 100. A timer capacitor 184 controls the rate of oscillation of the oscillator, and the oscillator is periodically turned on and off by an internal comparator in the converter 100. The internal comparator is connected to the junction 170 discussed above and compares the voltage generated at the junction 170 with an internally generated reference voltage. If the junction 170 voltage is lower than the reference voltage, the oscillator is enabled to oscillate. When the junction 170 voltage is higher than the reference voltage, the oscillator is disabled. Thus, the voltage at the junction 170 is controlled to match the internal reference voltage, and as a result the voltage on the capacitor 174 across the lines 20, 22 is controlled to the desired value of either about 20 or seven volts.

Now referring to FIG. 3, the warm-up of the sensor 12 is detected by sensing the voltage at the drain of a FET 190. The drain of the FET 190 is connected to a pair of resistors 192, 194, the junction of which is connected to the line 26 supplied to the noninverting input of the comparator 160 (FIG. 2). The inverting input of the comparator 160 is connected via the line 24 to a predetermined voltage as determined by a zener diode 198.

When the sensor 12 is not warmed up, the FET 190 drain voltage will be high, thus providing a relatively large voltage to the noninverting input of the comparator 160. As a result, the comparator 160 generates a high voltage which turns on the FET 162, thus placing a lower voltage at the junction 170, keeping the internal oscillator of the converter 100 on longer, and thus charging the capacitor 174 to a relatively high voltage of about 20 volts.

When the sensor 12 is warmed up, which may take approximately 15 seconds, the FET 190 drain voltage drops, thus providing a voltage to the noninverting input of the comparator 160 that is smaller than the predetermined voltage on the line 24. As a result, the comparator 160 generates a low output which turns off the FET 162, placing a higher voltage at the junction 170, turning off the internal oscillator of the converter 100 until the voltage across the capacitor reaches the lower value of about seven volts.

An advantage of reducing the voltage supplied to the current source 14 after the gas sensor is warmed up is that battery power is saved since less battery power is required to provide a lower voltage. As a result, the life of the batteries may be extended.

The power supply 19 also includes a resistor 202 and a capacitor 204 coupled across the output of the lines 20, 22. The resistor 202 and the capacitor 204 are provided for filtering purposes.

The current source 14 shown in FIG. 3 provides a constant current to the sensor 12 via the FET 190. The FET 190 is controlled by an operational amplifier 210. The inverting input of the amplifier 210 is provided with a predetermined voltage of approximately 330 millivolts (mv) due to its connection to the junction of a pair of resistors 212, 214 connected in parallel with the zener diode 198. The zener diode 198 is connected to a voltage regulator 220 which draws its power from the line 20.

During operation of the gas detector 10, current flows through the FET 190, the sensor 12, and a resistor 222. Although the resistors 192 and 194 are connected in parallel with the sensor 12 and the resistor 222, there is no appreciable current flow through the resistors 192, 194 since they have a very large resistance compared with the resistance of the sensor 12 and the resistor 222. Since substantially all of the sensor current flows through the resistor 222, the magnitude of the current can be determined by sensing the voltage across the resistor 222. For this purpose, the resistor 222 is connected to the noninverting input of the amplifier 210. In operation, the amplifier 210 controls the FET 190 so that the voltages provided on its noninverting and inverting inputs are substantially the same, about 330 mv. As a result, since the resistance of the resistor 222 is 10 ohms, the current through the sensor 12 is controlled to about 33 milliamperes.

The gas sensor 12 includes a reference thermistor 230 provided in a controlled environment, a sensing thermistor 232 provided in the outside environment to be tested, a resistor 234 and a resistor 236, all of which are connected in a bridge. The junction of the resistors 234 and 236 is connected to a potentiometer 238 so that the voltage between the resistors 234 and 236 may be adjusted.

In operation, the impedance of the sensing thermistor 232 changes in response to changes in density of the gas sensed, while the impedance of the thermistor 230 does not change in response to the gas. As a result, the voltage at the junction of the thermistors 230, 232 changes, and this variable voltage is provided to the amplifier 30 via the line 34. The voltage at the junction of the resistors 234, 236, which does not change during operation, is provided to the amplifier 30 via the line 36. The gas sensor 12, which may be any type of conventional gas sensor, may be a model HS-5 commercially available from Shibaura Electric Co., Ltd. of Saitama, Japan.

The variable and reference voltage signals generated by the gas sensor 12 are provided to the amplifier 30 via the lines 34, 36 respectively. The line 34 is connected to the noninverting input of an operational amplifier 250, and the line 36 is connected to the noninverting input of an operational amplifier 252. The two noninverting inputs of the amplifiers 250, 252 are also connected to a variable sensitivity circuit 256 comprising four parallel branches, each of the branches consisting of a series combination of a sensitivity resistor and a switch. The position of the four switches is controlled by the microprocessor 50 via the four lines 60, 62, 64, 66. When one of the switches is closed, the sensitivity resistor with which it is in series, is placed across the noninverting inputs of the amplifiers 250, 252. As a result, the sensitivity of the amplifiers 250, 252 can be adjusted.

The switches may be any type of conventional switches, such as transistors for example. Since there are four switches, there are sixteen different combinations of switch positions, thus providing 16 different sensitivity values for the amplifiers 250, 252. This discretely variable sensitivity advantageously allows the gas detector 10 to effectively sense and determine the concentration of different gases as described in more detail below Adjusting the amplifier sensitivity by changing the resistance across the noninverting inputs of the amplifiers 250, 252 is more advantageous than adjusting the gain of the amplifiers. This is due to the fact that adjusting the gain of the amplifiers may result in balancing problems which would require the gain of the amplifiers in each gas detector to be individually adjusted.

The inverting inputs of the two operational amplifiers 250, 252 are connected together via a resistor 254. The output of the amplifier 250 is connected to its inverting input via a resistor 258, and the output of the amplifier 252 is connected to its inverting input via a resistor 260. The values of the resistors 254, 258, 260 determine the gain of the amplifiers 250, 260, and thus the gain is a fixed, predetermined gain.

The amplifier 250 generates an output having a magnitude equal to the product of its gain and the difference between the signals provided on the lines 34, 36. The output of the amplifier 252 is equal in magnitude to the amplifier 250 output, but the output 252 is opposite in sign. The output of the amplifier 250 is provided to the inverting input of an operational amplifier 270 via a resistor 272 as well as the noninverting input of an operational amplifier 274 via a resistor 276. The output of the amplifier 252 is provided to the noninverting input of the amplifier 270 via a resistor 278 and to the inverting input of the amplifier 274 via a resistor 280. The noninverting inputs of the amplifiers 270, 274 are tied to a single reference voltage, Vref, via a pair of resistors 282, 284.

The output of the amplifier 270 is connected to its inverting input via a parallel connection of a capacitor 290 and a resistor 292. The output of the amplifier 274 is connected to its inverting input via a parallel connection of a capacitor 294 and a resistor 296. The gain of the amplifiers 270, 274, which is determined by the values of their associated elements, is a fixed, predetermined gain. Since the gain of each of the amplifiers 250, 252, 270, 274 is fixed, the overall gain of the amplifier circuit 30 is also fixed.

In response to the gas sensor's detection of gas, the analog outputs generated by the amplifiers 270, 274 on the lines 40, 42 change in magnitude by substantially the same amount in opposite directions about the central reference value, Vref. For example, when a particular concentration of gas is sensed, the output 40 might be about 3.0 volts, 0.5 volts above a reference value Vref of 2.5 volts, and the other output 42 might be about 2.0 volts, 0.5 volts below the reference value of 2.5 volts. If the concentration of the gas increases, the output 40 might rise further to 3.5 volts, while the output 42 would fall further to 1.5 volts. Thus, the outputs on the lines 40, 42 are opposite-going, and each has a magnitude based upon the concentration of the gas sensed. The outputs 40, 42 are generated substantially simultaneously with the sensing of the gas by the gas sensor 12.

The analog outputs on the lines 40, 42 are supplied to an A/D converter circuit 290. The A/D converter circuit 290 may comprise two separate A/D converters or different channels of the same A/D converter. For each of the signals input via the lines 40, 42, the A/D converter circuit 290 generates a binary count based upon the magnitude of the analog signal. The two binary counts are used to determine the concentration of the gas sensed as described in more detail below.

The gas detector 10 can be used to detect the presence and determine the concentration of a variety of different gases in a relatively simple manner. If a particular gas is to be sensed, the detector 10 is first calibrated with respect that gas, and then the detector can be used thereafter to sense that gas. To sense a different gas, the detector is recalibrated using a relatively simple procedure, and then it can detect the presence of that gas.

Figure 4:
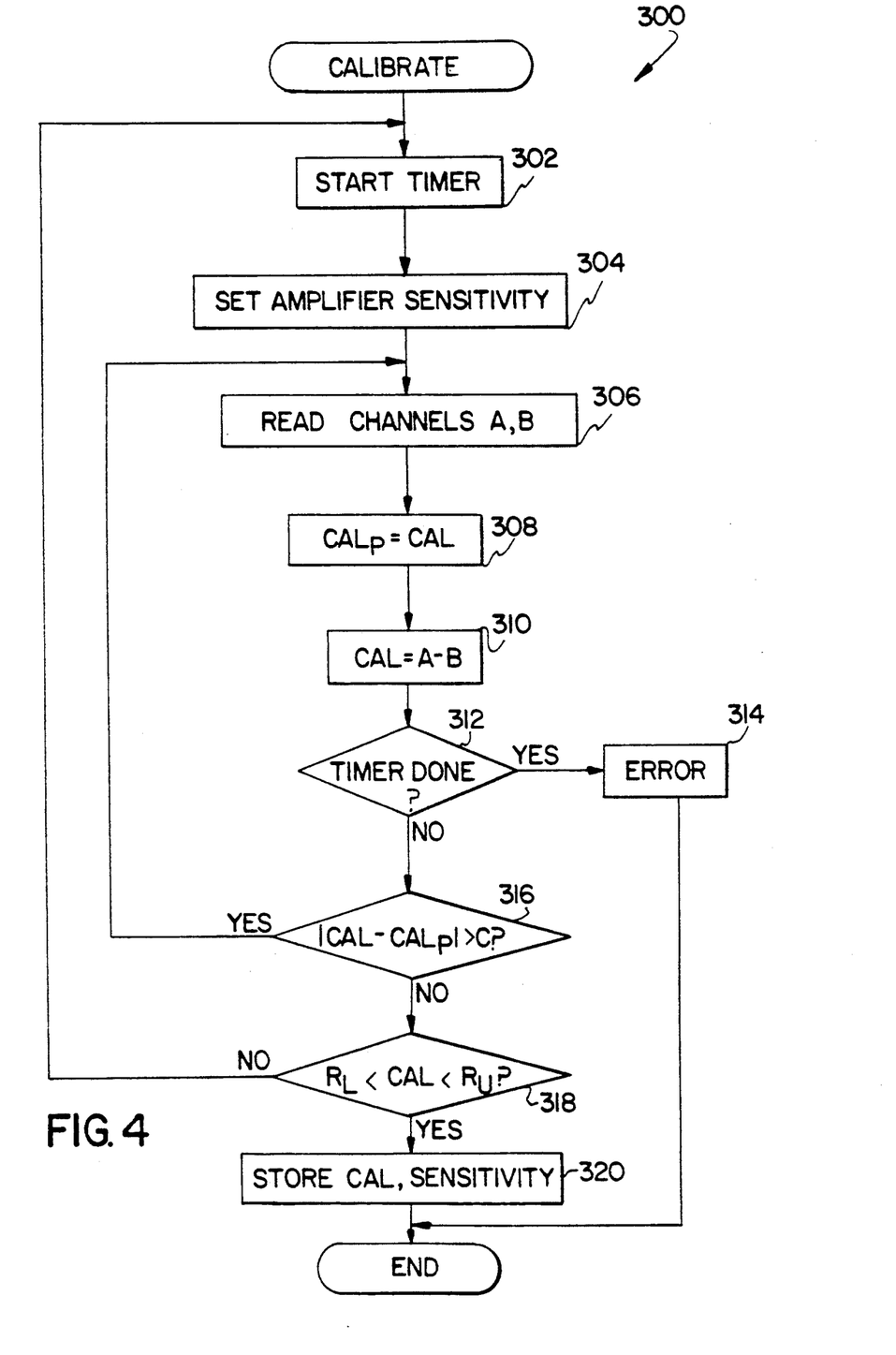
FIG. 4 is a flow chart of a calibration routine executed by the microprocessor of FIG. 1.

A flow chart of the operation of the detector 10 during the calibration procedure is shown in FIG. 4. Now referring to FIG. 4, a calibration routine 300 is shown. To calibrate it, the detector 10 is placed in a controlled environment containing a concentration of 100% of the gas for which the user desires to calibrate the device, such as 100% methane. The calibration routine may be initiated by the user by pressing a button (not shown). Initially, the calibration routine begins at step 302 by starting a timer, preferably a two-minute timer. At step 304, the sensitivity of the amplifier 30 is set by the microprocessor 50 by sending to the variable sensitivity circuit 256 an initial combination of four binary values which places the four switches in a first position. For example, the initial combination of four binary values may be arbitrarily chosen to be 0, 0, 0, 0 to place the four switches in their open positions so that no resistance is placed across the noninverting inputs of the amplifiers 250, 252.

At step 306, the two channels A and B of the A/D converter 290 are read, each of the channels generating a binary count stored in the variables A and B. At step 308, the current value of the variable CAL is stored in the variable $CAL_P$, which represents the value of CAL previously determined by the routine 300 (upon the initial execution of the routine 300, the values of CAL and $CAL_P$ are initialized to zero). The CAL variable, which stores the difference between the two binary counts stored in A and B, represents a calibration constant corresponding to a 100% concentration of the gas for which the detector is being calibrated. The calibration constant CAL is calculated at step 310 by subtracting the value of the B variable from the value of the A variable. At step 312, if the timer has timed out, the routine branches to an error state 314, generates an appropriate error message, and then terminates. Since the routine 300 is designed to take less than the timer period, the error state 314 is normally not reached.

Assuming the timer does not time out, the routine branches to step 316 where the absolute value of the difference between the CAL variable and the $CAL_P$ variable is tested to determine whether it is greater than a predetermined constant C. The purpose of step 316 is to ensure that the sensor 12 has stabilized, and that the current values of A and B, and thus CAL, are accurate. As the sensor 12 stabilizes, the values of A and B may vary, but will gradually settle to their correct values. During the routine 300, the A and B channels are repeatedly read and tested to determine whether their values have settled. When the difference between CAL, which represents the current difference between A and B, and $CAL_P$, which represents the previous difference between A and B, as determined at step 316 is greater than the constant C, the values of A and B are still changing significantly, indicating that the sensor has not stabilized. In this case, the routine branches from step 316 back to step 306 where the A and B channels will be read again.

If the difference between CAL and $CAL_P$ is not greater than C, the sensor 12 is considered to be stabilized, and CAL is assumed to accurately represent the calibration constant. In this case, the routine branches to step 318. The purpose of step 318 is to determine whether the present sensitivity of the amplifier 30 is set optimally. As described above, the initial setting of the amplifier sensitivity may be arbitrary. As a result, it is likely that the signal will not utilize the entire range of the A/D converter 290. For example, if an A/D converter having two 8-bit channels is used, the maximum possible difference between A and B would be $2^8$, or 256. This difference would use all of the resolution available from the two A/D channels. If the amplifier sensitivity were set so that the difference between A and B were 50, it would be desirable to increase the sensitivity so that a larger difference would be obtained in order to use all of the available resolution of the converter 290.

Accordingly, at step 318 if the value of CAL is not between a predetermined lower range value $R_L$ and a predetermined upper range value $R_U$, the sensitivity of the amplifier is not set optimally, and the routine branches back to step 302 where steps 302-318 will be repeated with a new amplifier sensitivity until the optimum sensitivity is found.

If CAL is between the limits $R_L$ and $R_U$, then the amplifier sensitivity is considered optimal, and the routine branches to step 320 where the value of CAL is stored in a nonvolatile memory 321 connected to the microprocessor 50. The nonvolatile memory 321 retains information even when the detector 10 is turned off. The four bit binary value used to set the switches of the variable sensitivity circuit is also stored in the memory 321 as the variable SENSITIVITY. These values of CAL and SENSITIVITY are later retrieved from the memory 321 for use in a sensing routine 400 described below.

Once the detector 10 is calibrated for a particular gas, the detector may be used to determine the concentration of that gas. Now referring to FIG. 5, a gas sensing routine 400 is executed upon power-up of the detector 10. The initial step 402 of the sensing routine 400 is to set the amplifier sensitivity in accordance with the value of SENSITIVITY that was stored in the memory 321 during the calibration routine described above.

Figure 5:
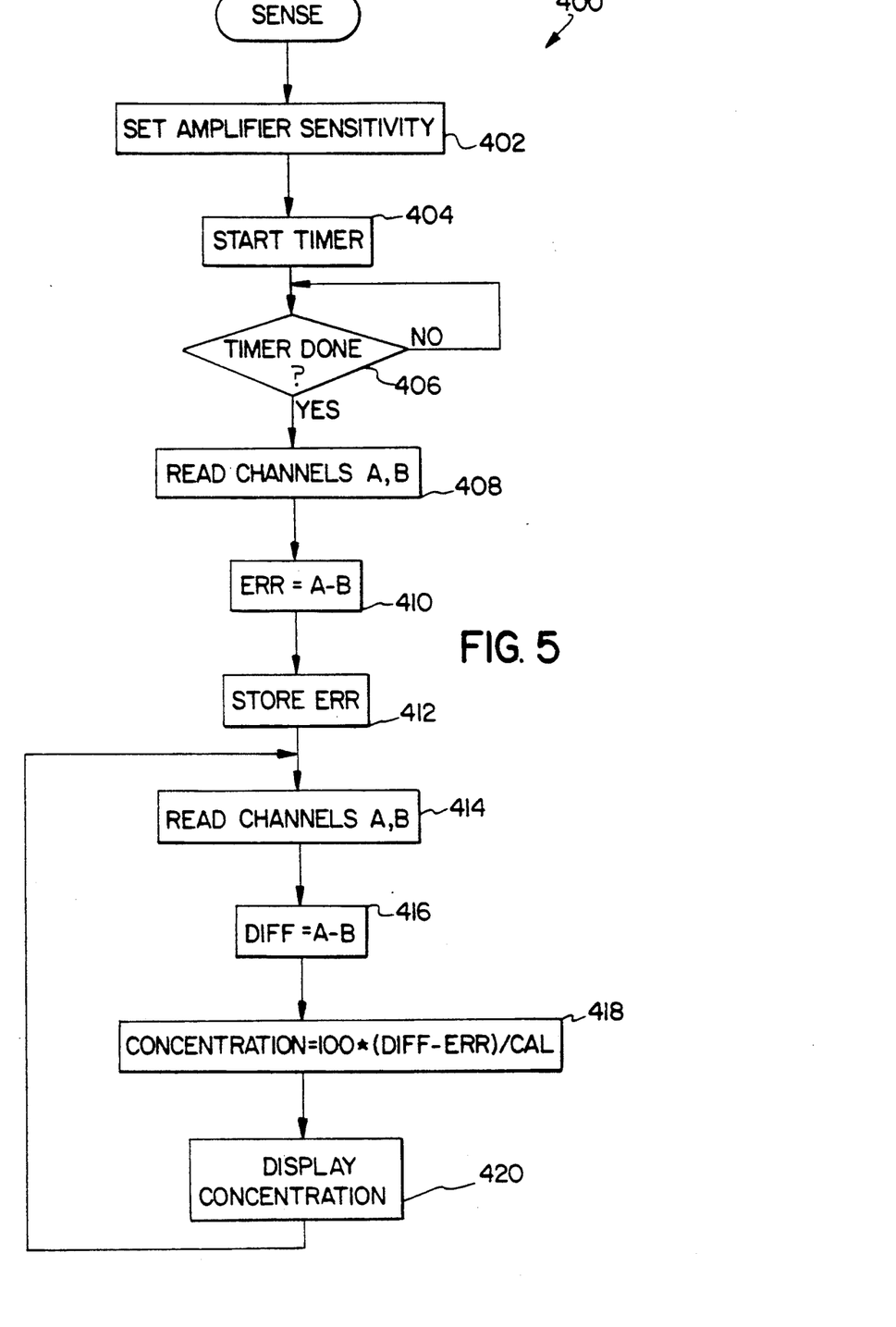
FIG. 5 is a flow chart of a gas sensing routine executed by the microprocessor of FIG. 1.

At step 404, a timer is started. The purpose of starting the timer is to wait a predetermined period of time, one minute for example, to allow the gas sensor 12 to warm up. If the predetermined period of time has elapsed as determined at step 406, the routine branches to step 408.

Steps 408-412 comprise an initial zeroing routine that is performed each time the detector 10 is turned on, when the detector is in an environment which has none of the gas that is to be measured present. For example, if attempting to determine whether there is a natural gas leak in a house, the detector should be turned on outside where no natural gas is present and should be kept there during the sensor warm-up period.

The zeroing routine determines the value of an error ERR between the two A/D converter channels, the magnitude of which depends primarily on temperature and humidity effects. For example, when the detector is in the outside environment with no gas present, the difference between the A and B channels should theoretically be zero. However, since the sensor 12 may be somewhat responsive to humidity, there may be a nonzero difference between A and B even with no gas present. Accordingly, the nonzero difference between A and B with no gas present is recorded as an error signal. Subsequently, when the detector is placed in the environment in which the gas is present, the magnitude of the error signal so determined is subtracted from the reading inside so that any humidity or temperature effects cancel and the reading inside relates only to the gas concentration present.

Thus, at step 408, the A and B channels of the A/D converter 290 are read; at step 410 the value of ERR is calculated by subtracting the binary count of B from the binary count of A; and at step 412 the value of ERR is stored in memory.

After the zeroing routine is executed with the detector in an environment with no gas present, the detector begins sensing for the presence of the gas during steps 414–420, which are continuously repeated. At step 414, the channels A and B are read, and at step 416 the difference between the A and B channels is stored in the DIFF variable. At step 418, the concentration of the gas is determined by subtracting the value of ERR from DIFF, dividing that difference by the calibration constant CAL, and then multiplying the result by 100 since the concentration is displayed as a percentage of gas present.

As an example, assume the calibration constant CAL is 240, meaning that an environment containing 100% gas would generate a difference between A and B of 240 binary counts. Also assume that the value of ERR is 15, meaning that in a no-gas environment the difference between A and B was 15 binary counts. Then if the difference DIFF between A and B in the gas-present environment was 45, the gas concentration would be 100 * (45−15)/240, or 12.5%.

The gas concentration so calculated is displayed on the visual display at step 420, and then the routine branches back to step 414 where channels A and B are again read and a new gas concentration determined. Steps 414–420 are repeated continuously until the detector 10 is turned off.

If it is desired that the zeroing routine of steps 402–412 to be repeated for any reason, the user may press a zeroing button (not shown), and the routine will branch to step 402, regardless of which step of the routine 400 is currently being performed.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A gas detector for sensing the presence of a gas and generating a signal relating to the concentration of the gas sensed, comprising:
    a gas sensor responsive to the presence of a gas;
    an amplifier circuit coupled to said gas sensor, said amplifier circuit generating a pair of signals having magnitudes which are related to the concentration of the gas sensed by said gas sensor;
    an A/D converter circuit coupled to said amplifier circuit to receive said signals, said A/D converter circuit generating a pair of binary counts based upon the magnitudes of said signals; and
    a difference circuit coupled to said A/D converter circuit that generates a signal relating to the concentration of the gas sensed based upon the difference between said pair of binary counts.

2. A gas detector as defined in claim 1 wherein said pair of signals generated by said amplifier circuit are opposite-going.

3. A gas detector as defined in claim 1 wherein said gas sensor comprises a bridge circuit.

4. A gas detector as defined in claim 1 wherein said difference circuit comprises a microprocessor.

5. A gas detector as defined in claim 1 wherein said A/D converter circuit comprises a single A/D converter having a first channel that receives one of said pair of signals generated by said amplifier circuit and a second channel that receives the other of said pair of signals generated by said amplifier circuit.

6. A gas detector as defined in claim 1 wherein said A/D converter circuit generates one of said pair of binary counts at substantially the same time as the other of said binary counts.

7. A gas detector for sensing the presence of a gas and generating a signal relating to the concentration of the gas sensed, comprising:
    a gas sensor responsive to the presence of a gas;
    an amplifier circuit coupled to said gas sensor, said amplifier circuit generating a pair of signals having magnitudes which are related to the concentration of the gas sensed by said gas sensor;
    an A/D converter circuit coupled to said amplifier circuit to receive said signals, said A/D converter circuit generating a pair of binary counts based upon the magnitudes of said signals; and
    a difference circuit coupled to said A/D converter circuit that generates a signal relating to the concentration of the gas sensed based upon the difference between said pair of binary counts.
    wherein said amplifier circuit comprises a first pair of operational amplifiers and a second pair of operational amplifiers, the output of each of said first pair of operational amplifiers being coupled to the input of each of said second pair of operational amplifiers.

8. A portable, battery-powered gas detector for sensing the presence of a gas, generating a signal relating to the concentration of the gas sensed, and providing a visual indication of the concentration of the gas sensed, said gas detector comprising:
    a gas sensor responsive to the presence of a gas, said gas sensor comprising a bridge circuit having four corners;
    an amplifier circuit coupled to said gas sensor, said amplifier circuit generating a pair of signals whose magnitudes are related to the concentration of the gas sensed by said gas sensor, said amplifier circuit comprising:

a first amplifier coupled to a first of said corners of said bridge circuit;

a second amplifier coupled to a second of said corners of said bridge circuit;

a third amplifier coupled to both of said first and second amplifiers; and a fourth amplifier coupled to both of said first and second amplifiers;

a power supply coupled to a third and a fourth of said corners of said bridge circuit;

a pair of battery terminals coupled to said power supply;

an A/D converter circuit coupled to said amplifier circuit to receive said signals from said amplifier circuit, said A/D converter circuit generating a pair of binary counts based upon the magnitude of said signals;

a difference circuit coupled to said A/D converter circuit that generates a signal relating to the concentration of the gas sensed based upon the difference of said pair of binary counts; and an indicator coupled to said difference circuit that provides a visual indication of the concentration of the gas sensed.

9. A gas detector as defined in claim 8 wherein said power supply comprises a DC/DC converter.

10. A portable, battery-powered gas detector for determining the concentration of a plurality of different gases, said gas detector comprising:

a gas sensor responsive to the presence of a gas, said gas sensor comprising a bridge circuit having four corners;

an amplifier circuit coupled to said gas sensor, said amplifier circuit generating a pair of signals whose magnitudes are related to the concentration of the gas sensed by said gas sensor, said amplifier circuit comprising:

a first amplifier coupled to a first of said corners of said bridge circuit;

a second amplifier coupled to a second of said corners of said bridge circuit;

a third amplifier coupled to both of said first and second amplifiers;

a fourth amplifier coupled to both of said first and second amplifiers; and means for automatically changing the sensitivity of at least one of said amplifiers whereby the gas detector can be used to determine the concentration of a plurality of different gases;

a power supply coupled to a third and a fourth of said corners of said bridge circuit;

a pair of battery terminals coupled to said power supply;

an A/D converter circuit coupled to said amplifier circuit to receive said signals from said amplifier circuit, said A/D converter circuit generating a pair of binary counts based upon the magnitude of said signals;

a difference circuit coupled to said A/D converter circuit that generates a signal relating to the concentration of the gas sensed based upon the difference of said pair of binary counts; and an indicator coupled to said difference circuit that provides a visual indication of the concentration of the gas sensed.

11. A method of sensing gas comprising the steps of:
(a) sensing the presence of a gas;
(b) generating a pair of opposite-going signals each of which relates to the concentration of the gas sensed;
(c) determining the magnitude of the difference between said opposite-going signals; and
(d) generating an indication relating to the concentration of the gas sensed based upon the magnitude of the difference between said opposite-going signals.

12. A gas detector for sensing the presence of a gas and generating a signal relating to the concentration of the gas sensed, said gas detector also being capable of determining the concentration of a plurality of different gases, said gas detector comprising:

a gas sensor responsive to the presence of a gas;

an amplifier circuit coupled to said gas sensor, said amplifier circuit generating a first signal having a magnitude which is related to the concentration of the gas sensed by said gas sensor;

means coupled to said amplifier circuit for automatically changing the sensitivity of said amplifier circuit whereby the concentrations of a plurality of different gases can be determined by said gas detector;

an A/D converter circuit coupled to said amplifier circuit to receive said signal, said A/D converter circuit generating a binary count based upon the magnitude of said signal; and a circuit coupled to said A/D converter circuit that generates a second signal relating to the concentration of the gas sensed.

13. A gas detector for sensing the presence of a gas and generating a signal relating to the concentration of the gas sensed, said gas detector also being capable of determining the concentration of a plurality of different gases, said gas detector comprising:

a gas sensor responsive to the presence of a gas;

an amplifier circuit coupled to said gas sensor, said amplifier circuit generating a first signal having a magnitude which is related to the concentration of the gas sensed by said gas sensor;

means coupled to said amplifier circuit for automatically changing the sensitivity of said amplifier circuit whereby the concentrations of a plurality of different gases can be determined by said gas detector;

an A/D converter circuit coupled to said amplifier circuit to receive said signal, said A/D converter circuit generating a binary count based upon the magnitude of said signal; and a circuit coupled to said A/D converter circuit that generates a second signal relating to the concentration of the gas sensed, wherein said means for automatically changing the sensitivity of said amplifier circuit comprises:

a plurality of switches coupled in series with a plurality of resistors; and means for selectively turning said switches off and on to provide a plurality of discrete sensitivities for said amplifier circuit.

14. A gas detector for sensing the presence of a gas and generating an indication of the concentration of the gas sensed, comprising:

a gas sensor responsive to the presence of a gas;

an amplifier circuit coupled to said gas sensor, said amplifier circuit generating a pair of signals having magnitudes which are related to the concentration of the gas sensed by said gas sensor;

an A/D converter circuit coupled to said amplifier circuit to receive said signals, said A/D converter circuit generating a pair of binary counts based upon the magnitudes of said signals;

a difference circuit coupled to the output of said A/D converter circuit that generates a signal relating to the concentration of the gas sensed based upon the difference between said pair of binary counts; and an indicator that provides an indication of the concentration of the gas sensed.

15. A gas detector as defined in claim 14 wherein said difference circuit comprises a microprocessor.

16. A gas detector as defined in claim 14 wherein said signals generated by said amplifier circuit are opposite-going.

17. A gas detector as defined in claim 16 wherein said signals generated by said amplifier circuit change in magnitude by substantially the same amount in opposite directions about a central value.

18. A gas detector as defined in claim 14 wherein said gas detector is portable and battery-powered.

19. A gas detector as defined in claim 14 wherein said gas sensor comprises a bridge circuit.

20. A gas detector as defined in claim 14 wherein said amplifier circuit comprises a pair of operational amplifiers.

21. A gas detector as defined in claim 20 wherein said amplifier circuit additionally comprises a second pair of operational amplifiers.

22. A gas detector as defined in claim 14 additionally comprising means for automatically changing the sensitivity of said gas detector.

23. A gas detector as defined in claim 22 wherein said means for automatically changing the sensitivity of said gas detector comprises:

a plurality of switches coupled in series with a plurality of resistors; and means for selectively turning said switches off and on to provide a plurality of discrete sensitivities for said amplifier.

* * * * *